(12) United States Patent
Bryson

(10) Patent No.: US 11,292,765 B2
(45) Date of Patent: Apr. 5, 2022

(54) TRYPTAMINE PRODRUGS

(71) Applicant: Field Trip Psychedelics Inc., Toronto (CA)

(72) Inventor: Nathan Bryson, Toronto (CA)

(73) Assignee: Field Trip Psychedelics Inc., Toronto (CA)

(*) Notice: Subject to any disclaimer, the term of this patent is extended or adjusted under 35 U.S.C. 154(b) by 0 days.

(21) Appl. No.: 17/364,047

(22) Filed: Jun. 30, 2021

(65) Prior Publication Data

US 2021/0403425 A1   Dec. 30, 2021

Related U.S. Application Data

(60) Provisional application No. 63/045,901, filed on Jun. 30, 2020, provisional application No. 63/109,095, filed on Nov. 3, 2020.

(51) Int. Cl.

| *C07D 209/16* | (2006.01) |
|---|---|
| *C07D 209/08* | (2006.01) |
| *A61K 9/08* | (2006.01) |
| *A61K 9/00* | (2006.01) |
| *A61K 9/20* | (2006.01) |

(52) U.S. Cl.
CPC .......... *C07D 209/16* (2013.01); *A61K 9/0019* (2013.01); *A61K 9/0053* (2013.01); *A61K 9/08* (2013.01); *C07D 209/08* (2013.01); *A61K 9/20* (2013.01)

(58) Field of Classification Search
CPC .................................................. C07D 209/16
See application file for complete search history.

(56) References Cited

U.S. PATENT DOCUMENTS

| 3,075,992 A | 1/1963 | Hofmann et al. |
| 2022/0017549 A1 | 1/2022 | Slassi et al. |
| 2022/0024956 A1 | 1/2022 | Slassi et al. |

FOREIGN PATENT DOCUMENTS

| WO | 9506638 A1 | 9/1995 |
| WO | 2006047032 A2 | 4/2006 |
| WO | 2020181194 A1 | 10/2020 |
| WO | 2021155470 A1 | 12/2021 |

OTHER PUBLICATIONS

Il'ina et al. CAS: 83: 201816, 1975.*
Makhaeva et al. CAS: 83: 113322, 1975.*
International Search Report, dated Oct. 20, 2021, in International application No. PCT/CA2021/050907, filed on Jun. 30, 2021 (4 pages).
Makhaeva et al., "Synthesis and kinetics of the hydrolysis of serotonin terephthalates and succinates." Zhurnal Organicheskoi Khimii, 1975, vol. 11(7) 1489-1498, * compounds 1a and 1b, Scheme 1, p. 1489 *.
Database CAS Chemcats [Online], "1,4-Benzenedicarboxylic acid, 1-[3-(2-aminoethyl)-1H-indol-4-yl] ester," Chemical Abstracts Service, Columbus, OH, USA. STN entry date Aug. 17, 2006 (Aug. 17, 2006), Retrieved from STN, CAS RN: 902412-24-2.
Database CAS Registry [Online], "Hexanedioic acid, 1-[3-2-aminoethyl)-1H-indol-5-yl] ester," Chemical Abstracts Service, Columbus, OH USA. STN entry date Nov. 16, 1984 (Nov. 16, 1984), Retrieved from STN, CAS RN: 33598-45-7.
Database CAS Chemcats [Online], "2-Butenedioic acid, 1-[3-(2-aminoethyl)-1H-indol-5-yl] ester," Chemical Abstracts Service, Columbus, OH, USA. STN entry date Nov. 19, 2020 (Nov. 19, 2020), Retrieved from STN, CAS RN: 2519519-21-0, Retrieved from STN, CAS RN: 2519519-21-0.
Glennon et al., "Butofenine Esters," Journal of Medicinal Chemistry, 1979, vol. 22(11), pp. 1414-1416.
Glennon et al., "Synthesis and Evaluation of a Novel Series of N,N-Dimethylisotryptamines." Journal of Medicinal Chemistry, 1984, vol. 27(1), pp. 41-45.
Troxler et al., "Synthetic indole compounds. II. Psilocybin and psilocin modifications." Helvetica Chimica Acta, 1959, vol. 42, pp. 2073-2103.
Certified priority document for U.S. Appl. No. 62/969,934, filed Feb. 4, 2020.

* cited by examiner

*Primary Examiner* — Rei Tsang Shiao
(74) *Attorney, Agent, or Firm* — Michael Stanley Tomsa; McAndrews, Held & Malloy, Ltd.

(57) ABSTRACT

The present invention provides a tryptamine prodrug compound. A compound represented by the formula (I)

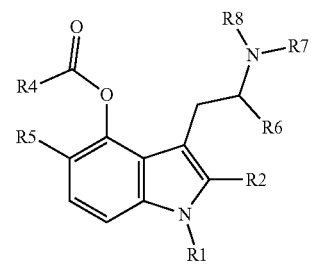

where each symbol is as described in the specification, or a salt or zwitterion thereof, is converted to an active which has 5HT2A receptor agonist activity, and is useful as an agent for the treatment of depression.

23 Claims, 1 Drawing Sheet

TRYPTAMINE PRODRUGS

CROSS-REFERENCE TO RELATED APPLICATIONS

This application claims priority to U.S. Provisional Application Ser. No. 63/045,901 filed on Jun. 30, 2020, entitled "TRYPTAMINE PRODRUGS", and to U.S. Provisional Application Ser. No. 63/109,095 filed on Nov. 3, 2020, entitled "TRYPTAMINE PRODRUGS". The entire contents of U.S. Provisional Application Ser. No. 63/045,901 and U.S. Provisional Application Ser. No. 63/109,095 are hereby incorporated by reference in this application.

FIELD OF THE INVENTION

The present invention relates to novel tryptamine compounds, methods of making and using such compounds, compositions comprising such compounds, and their uses.

BACKGROUND

Tryptamines are a class of 3-aminoethyl-indoles that bind and activate the serotonin receptor, also called the 5HT receptor. A psychedelic state may be achieved by activation of the 2A form of the serotonin receptor by 5HT2A receptor agonist compounds. The endogenous substance for this receptor is 5-hydroxy-tryptamine (serotonin). The tryptamine 3-(2-aminoethyl)-indole is also an endogenous neurotransmitter.

The serotonin receptor system is implicated in depression and depressive states which are commonly treated with 5HT1A antagonists (Affective Disorders: Depression in Neuropsychopharmacology and Therapeutics, Chapter 6, First Edition. Ivor S. Ebenezer, 2015). More recently, 5HT2A agonists have shown potential as medicines for depression (Carhart-Harris 2018 Psychopharmacology).

Tryptamine molecules which produce a psychedelic state and which have been used in traditional medicine, may have therapeutic potential for the treatment of mood disorders, distress, depression and others. For example, ayahuasca is a natural form of dimethyltryptamine (DMT) which when combined with a monoamine oxidase inhibitor can be ingested and produces a variable, but prolonged psychedelic state that can last for 6 to 15 hours. DMT is also naturally found to occur in small amounts in the brain and may act as a neurotransmitter.

Lysergic acid diethylamide (LSD), is a diethylamide derivative of a naturally occurring substance from fungus found in rye grain, which also produces a prolonged psychedelic state up to 8 to 12 hours long.

Psilocybin is a naturally occurring plant-based tryptamine found in Psilocybe mushrooms, and produces a prolonged psychedelic state of about 6 to 8 hours. Psilocybin was first synthesized in 1958 and is currently being investigated as a treatment for depression. Psilocybin is a prodrug, with psilocin being the active species in vivo. Psilocybin contains a phosphate bound to the 4-hydroxy group of psilocin, which is cleaved in the gut when Psilcybe mushrooms or the drug substance is taken orally:

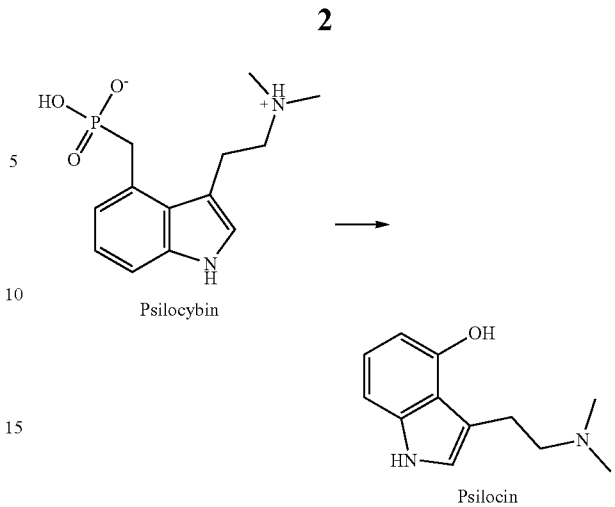

Simple mono-functional organic esters of psilocin have been reported. Lower alkoxy radical modified psilocins have also been described. Sulfate-bound psilocin has been produced and other mono- and di-basic mineral acid modified psilocins have been described. Psilocin acetate is known and has been used in underground psychedelic subculture.

Psychedelic substances have been shown to be effective for treating depression, and even more effective for treating depression when associated with psychotherapy (Watts 2020 J Contextual Behavioral Science).

A limited number of synthetic tryptamine substances have been prepared since perhaps the earliest recorded work of Albert Hoffman. Structure-activity relationships have been described for a variety of tryptamine substances (Claire 1988).

Succinate and other diacid functions have been explored as components of a prodrug delivery system toward water-soluble, injectable forms of hydrophobic or poorly water soluble drug substances, such as testosterone, haloperidol, chloramphenicol or estradiol (Silverman and Holladay, Chapter 9.2: Prodrugs and Drug Delivery Systems in The Organic Chemistry of Drug Design and Drug Action ($3^{rd}$ Ed), 2014). Tetrahydrocannabinol ester of succinic acid has been patented to treat glaucoma. However, ester cleavage is not consistently rapid, is not predictable and can depend on the structure of the moiety attached to the drug and therefore must be investigated (Anderson 1984 JPharmaSci). Esterase enzymes are responsible for active cleavage of the prodrug ester group in vivo and species differences in esterase quantities and specificity in various tissues complicate investigations and optimizations (Bahar 2012 JPharmSci).

This background information is believed to be relevant to a basic understanding of the present invention. It is not an admission that any of the foregoing is prior art against any aspect of the claimed invention.

SUMMARY OF THE INVENTION

The present invention relates to novel tryptamine compounds, which when administered, convert to an active form in vivo, and act as a 5HT2A agonist. The compounds described herein may be useful to treat mental disorders, such as a depressive condition, including unipolar and bipolar depressive conditions, such as but not limited to depression, depression from generalized anxiety, major depression, treatment resistant depression and postpartum depression.

In one aspect, the present invention relates to a tryptamine or isotryptamine compound of Formula (I) (II), (III) or (IV) or a pharmaceutically acceptable salt or zwitterion thereof:

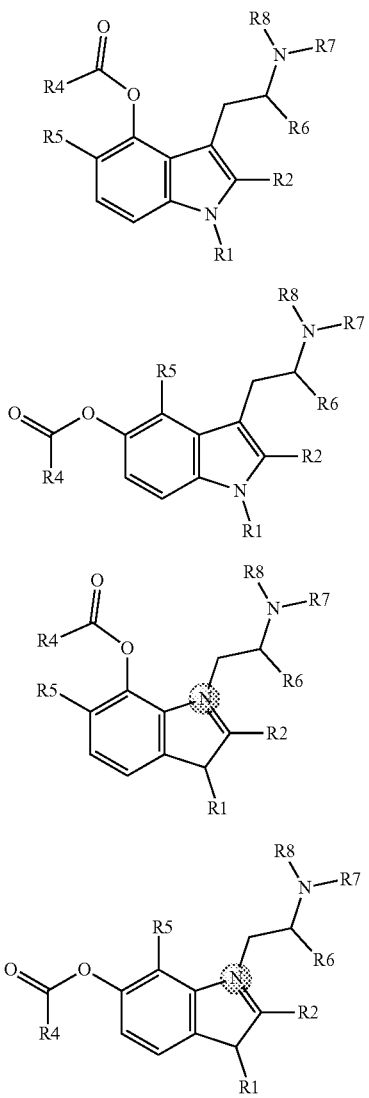

wherein:
(1) R1, R2, and R6 are each independently selected from hydrogen, linear or branched alkyl, preferably $C_{1-5}$ alkyl, or arylalkyl;
(2) R4 is
   a. —X—CO2H, where X is a linear, cyclic or branched, saturated or unsaturated carbon chain (preferably $C_{1-5}$ alkyl), optionally substituted with —OH or —CO2H, or an aromatic ring, optionally substituted with alkyl or CO2H; or
   b. (R9)(R10)N—, wherein R9 is X—CO2H, where X is defined as above, and R10 is hydrogen, linear or branched alkyl (preferably $C_{1-5}$ alkyl) or arylalkyl, optionally substituted by —OH or —CO2H;
(3) R5 is hydrogen, linear or branched alkyl (preferably $C_{1-5}$ alkyl), arylalkyl, or O—R5', where R5' is hydrogen, linear or branched alkyl (preferably $C_{1-5}$ alkyl); and (4) R7 and R8:
   a. are each independently selected from hydrogen, linear or branched alkyl (preferably $C_{1-5}$ alkyl), or arylalkyl, or
   b. together form a non-aromatic N-containing heterocycle, optionally substituted with alkyl, preferably where the entire heterocyclic structure does not contain more than 12 atoms.

In another aspect, the invention comprises diacid esters of a hydroxytryptamine, such as 4-hydroxy and 5-hydroxytryptamines and 6-hydroxy and 7-hydroxy isotryptamines, and other structural or functional analogs of psychedelic tryptamines.

In some embodiments, R7 and R8 are the same or different, and are linear or branched $C_{1-4}$ alkyl; or are the same or different, and are methyl or isopropyl; such as R7 and R8 are both methyl, or R7 and R8 are both isopropyl, or where one of R7 and R8 is methyl and the other is isopropyl.

In some embodiments, X is a linear C1-C3 chain, optionally substituted with OH or —CO2H, such as X is an unsubstituted linear C3 chain.

In another aspect, the invention relates to a composition comprising a compound described herein, and a pharmaceutically acceptable excipient. In some embodiments, the composition comprises an oral dosage formulation or an injectable formulation.

In another aspect, the invention comprises a method of treating a mental disorder, comprising the step of administering an effective amount of a compound described herein. In some embodiments, the mental disorder is a depressive condition, including unipolar and bipolar depressive conditions, such as but not limited to depression, depression from generalized anxiety, major depression, treatment resistant depression and postpartum depression.

In another aspect, the invention relates to the use of a compound described herein to treat a mental disorder, or in the manufacture of a medicament for treating a mental disorder, such as depression.

In another aspect, the invention relates to a method of making a compound described herein, comprising reacting a tryptamine comprising a hydroxytryptamine or hydroxyisotryptamine with a cyclic anhydride in a suitable anhydrous solvent. In some embodiments, the solvent contains a base with pKa greater than 4 but less than 9, and the resulting compound is isolated as a zwitterion. In some embodiments, the tryptamine comprises 4-hydroxy or 5-hydroxy tryptamine or a 6-hydroxy or 7-hydroxy isotryptamine. In some embodiments, the solvent is pyridine.

DETAILED DESCRIPTION

Figure 1:
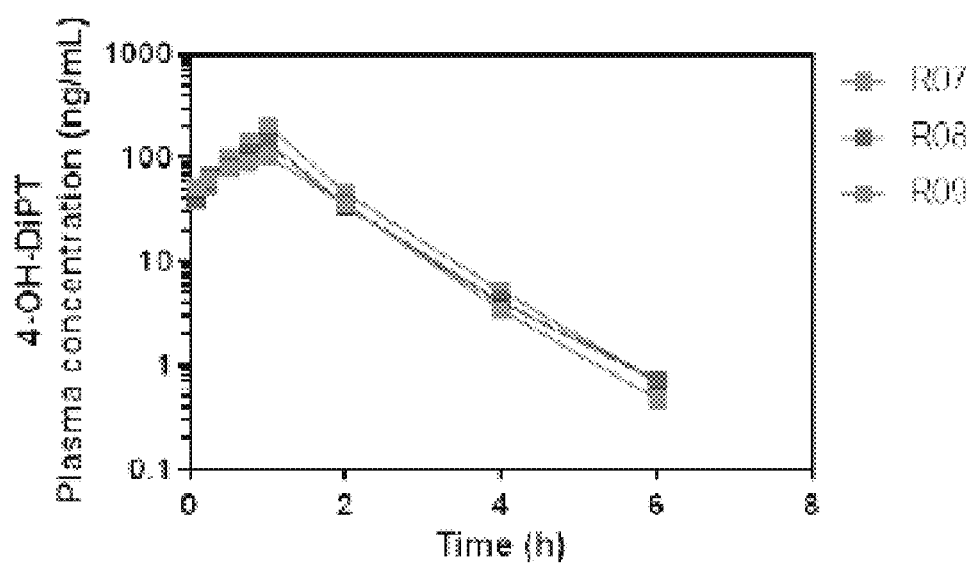
FIG. 1 is a graph showing plasma concentration of 4-HO-DiPT (ng/ml) time after subcutaneous administration of N,N diisopropyltryptamine-4-glutarate at a rate of 2 mg/kg.

Embodiments of the present invention comprise novel synthetic tryptamine prodrugs. The prodrugs may be useful for treatment of mental disorders such as depression, including without limitation, major depression, treatment resistant depression and postpartum depression. As used herein, the term "mental disorder" includes those disorders which may be diagnosed by a mental health professional as a psychological or psychiatric disorder, including those which may be diagnosed by reference to Diagnostic and Statistical Manual of Mental Disorders (DSM-5).

The term "treating", "treat" or "treatment" as used herein embraces both preventative, i.e., prophylactic, and palliative treatment, i.e., relieve, alleviate, or slow the progression of the patient's disease, disorder or condition.

As used herein, "psychedelic state" is an altered state of consciousness experienced by a person, which may include intensified sensory perception, perceptual distortion or hallucinations, and/or feelings of euphoria or despair. Psychedelic states have been described as resulting from psychedelic drugs such as DMT (dimethyltryptamine), LSD, mescaline or psilocybin. Other known psychedelic drugs include the 4-hydroxy analogs of N-Methyl-N-isopropyl-tryptamine (MiPT) and N,N-diisopropyltryptamine (DiPT).

The present invention comprises prodrugs of hydroxy-indole 5HT2A agonists which induce a psychedelic state or which still provide a beneficial therapeutic effect without being associated with a psychedelic state. The prodrugs may be used in combination with other treatments known to be effective for treating mental disorders, such as psychotherapy, electroconvulsive therapy and/or other pharmaceutical compounds, for example, with concomitant use of tricyclic antidepressants (TCAs), selective serotonin reuptake inhibitors (SSRIs), selective norepinephrine reuptake inhibitors (SNRIs), monoamine oxidase inhibitors (MOAIs) or other anti-depressants. In preferred embodiments, the treatment may produce lasting effects, for example longer than 1 month after a single treatment, preferably longer than 3 months, and more preferably longer than 6 months. In some embodiments, additional therapy may not be required.

Compounds

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug (or "active") in vivo via some chemical or physiological process (e.g., hydrolysis, enzymatic cleavage or hydrolysis, or metabolism is converted to the desired drug form). The invention includes within its scope the pharmaceutically acceptable salts of the compounds of the invention. Accordingly, the phrase "or a pharmaceutically acceptable salt thereof" is implicit in the description of all compounds described herein unless explicitly indicated to the contrary.

In some embodiments, the compounds of the present invention comprise prodrug compounds that are readily purified, formulated and stable, and preferably may be used to provide highly soluble drug substances, with fast onset and elimination for convenient use in a clinical setting. In some embodiments, the compounds may be produced as a zwitterion, which may be converted to a pharmaceutically acceptable salt.

In some embodiments, the compounds of the present invention preferably allow for fast cleavage in vivo of the prodrug moiety to give the active pharmacophore, for example, 90% conversion may occur in under 4 hours, preferably in less than 2 hours, and more preferably in less than 1 hour. Prodrugs may have lesser, little or no pharmacological activity themselves, however when administered to a patient, may be converted into an active compound, for example, by hydrolytic cleavage.

Diacid hemiesters of tryptamines, such as psilocin or other hydroxytryptamines or isotryptamines, have not previously been described. A prodrug strategy implemented by combining a diacid and a 4-hydroxy-tryptamine or 5-hydroxy-tryptamine has likely not been proposed, as a prodrug strategy is typically not necessary when the drug is already soluble. Therefore, aspects of this diacid hemiester prodrug strategy, as described herein, are believed to be novel and inventive.

In one aspect, the present invention comprises a tryptamine or isotryptamine compound of Formula (I) (II), (III) or (IV), or a pharmaceutically acceptable salt or zwitterion thereof:

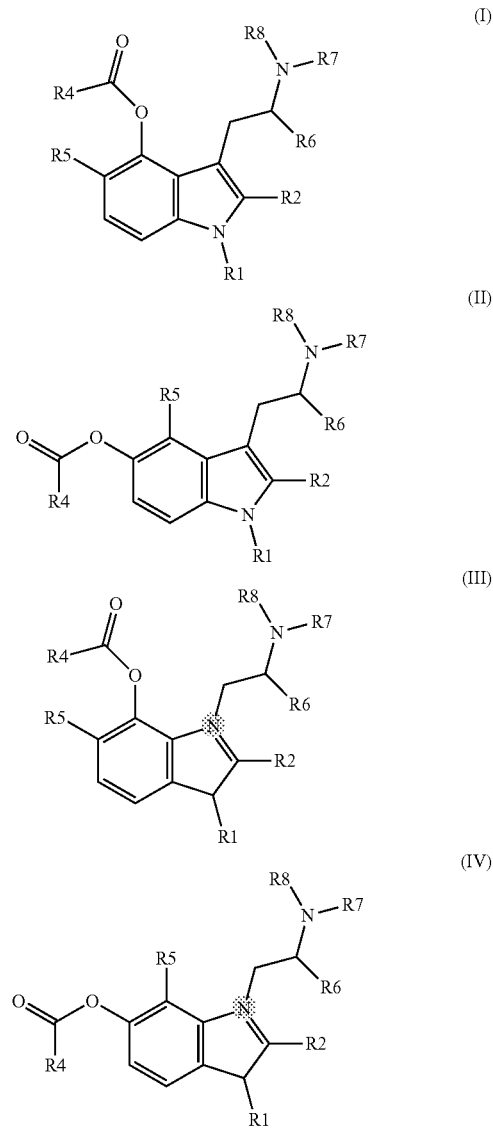

wherein:
(1) R1, R2, and R6 are each independently selected from hydrogen, linear or branched alkyl, preferably $C_{1-5}$ alkyl, or arylalkyl;
(2) R4 is
   a. —X—CO2H, where X is a linear, cyclic or branched, saturated or unsaturated carbon chain (preferably C$_{1-5}$ alkyl), optionally substituted with —OH or —CO2H, or an aromatic ring, optionally substituted with alkyl or CO2H; or b.

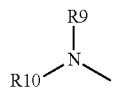

wherein R9 is X—CO2H, where X is as defined (2)(a) above and R10 is hydrogen, linear or branched alkyl (preferably C$_{1-5}$ alkyl) or arylalkyl, optionally substituted by —OH or —CO2H;

(3) R5 is hydrogen, linear or branched alkyl (preferably C$_{1-5}$ alkyl), arylalkyl, or O—R5', where R5' is hydrogen, linear or branched alkyl (preferably C$_{1-5}$ alkyl); and (4) R7 and R8:
  a. are each independently selected from hydrogen, linear or branched alkyl (preferably C$_{1-5}$ alkyl), or arylalkyl, or
  b. together form a non-aromatic N-containing heterocycle, optionally substituted with alkyl, preferably where the entire heterocyclic structure does not contain more than 12 atoms, for example, pyrrolidine (NC4 ring) piperidine (NC5 ring), or morpholine (NC4O ring).

"Alkyl," by itself or as part of another substituent, refers to a saturated branched, straight-chain or cyclic monovalent hydrocarbon radical derived by the removal of one hydrogen atom from a single carbon atom of a parent alkane. The term "alkyl" includes cycloalkyl. Typical alkyl groups include, but are not limited to, methyl; ethyl; propyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, an alkyl group comprises from 1 to 20 carbon atoms (C$_1$-C$_{20}$ alkyl). In other embodiments, an alkyl group comprises from 1 to 10 carbon atoms (C$_1$-C$_{10}$ alkyl). In still other embodiments, an alkyl group comprises from 1 to 6 carbon atoms (C$_1$-C$_6$ alkyl) or 1 to 4 carbon atoms (C$_1$-C$_4$). C$_1$-C$_6$ alkyl is also known as "lower alkyl".

The term "arylalkyl" is a term of the art and as used herein refers to an alkyl group, for example a C$_{1-6}$ alkyl group, substituted with an aryl group, where the residue is linked to the main molecule through the alkyl group. An example of arylalkyl is the benzyl group, that is, the phenyl-methyl group.

"Substituted," when used to modify a specified group or radical, means that one or more hydrogen atoms of the specified group or radical are each, independently of one another, replaced with the same or different substituent(s). The term "substituted" specifically envisions and allows for one or more substitutions that are common in the art. However, it is generally understood by those skilled in the art that the substituents should be selected so as to not adversely affect the useful characteristics of the compound or adversely interfere with its function.

The term "optionally substituted" denotes the presence or absence of the substituent group(s). That is, it means "substituted or unsubstituted". For example, optionally substituted alkyl includes both unsubstituted alkyl and substituted alkyl. The substituents used to substitute a specified group can be further substituted, typically with one or more of the same or different groups selected from the various groups specified above.

These prodrug structures are converted to an active hydroxy-indole 5HT2A agonist after hydrolysis or metabolization of the ester function R4-CO—.

In some non-limiting examples, the compounds comprise diacid esters of tryptamine structures such as 4-hydroxy-N,N-dimethyltryptamine (psilocin or 4-HO-DMT), 4-hydroxy-N,N-diethyltryptamine (4-HO-DET), 4-hydroxy-N,N-diisopropyltryptamine (4-OH-DiPT), 4-hydroxy-N-methyl-N-isopropyltryptamine (4-OH-MIPT), 5-hydroxy-N,N-dimethyltryptamine, 4-methyl-5-hydroxy-N,N-dimethyl) tryptamine and 4-hydroxy-5-methyl-N,N-dialkyltryptamine. In some embodiments, the compounds include the 4- and 5-substituted hemisuccinates, hemiglutarates and citrates of 4-hydroxy derivatives of N,N-dimethyltryptamine (psilocin), N,N-diisopropyltryptamine (4-HO-DiPT), or N-methyl-N-isopropyl-tryptamine (4-HO-MiPT).

In some embodiments, the compound comprises a compound of Formula I, II, III or IV, wherein R1, R2, R5, R6, are each hydrogen; X is a linear C1-4 alkyl; and R7 and R8 are each methyl. In a preferred embodiment, the compound is a compound of Formula I or II and X is C2 alkyl, thus forming a 4- or 5-hemisuccinate of psilocin.

In some embodiments, the compound comprises a compound of Formula I, II, III or IV, wherein R1, R2, R5, R6, are each hydrogen; X is a linear C1-C4 alkyl chain; and R7 and R8 are each isopropyl. In some embodiments, the compound is a compound of Formula I or II, X is C2 alkyl, thus forming a hemisuccinate of 4- or 5-hydroxy-diisopropyltryptamine. In some embodiments, the compound is a compound of Formula I or II, X is a C2 alkene, thus forming a hemifumarate of 4- or 5-hydroxy-diisopropyltryptamine. In some embodiments, the compound is a compound of Formula I or II and X is a C3 alkyl chain, thus forming a hemiglutarate of 4- or 5-hydroxy-diisopropyltryptamine.

In some embodiments, R7 and R8 are each chosen on the basis of retaining or enhancing the compound's ability to induce a psychedelic state. It is known that psychedelic activity of a tryptamine is reduced if R7 or R8 become larger than C4. However, such compounds are still within the scope of the present invention if they are still 5HT2A agonists which can produce beneficial therapeutic effect without a psychedelic state.

In some embodiments, compounds of the present invention are diacid zwitterions. Thus, where X is a linear saturated alkyl, the diacid may comprise a common linear alkyl α,ω-diacid, including without limitation oxalic, malonic, succinic, glutaric (pentanedioic), adipic (hexanedioic), pimelic (heptanedioic) and suberic acid (octanedioic). In some embodiments, where X is a linear alkene, the diacid may comprise an acid such as maleic, fumaric, or glutaconic acid. In other embodiments, the diacid may comprise a branched acid such as citraconic, mesaconic, 2,2-dimethylsuccinic acid; a substituted acid such as tartronic, 2-(2-hydroxyethyl)-malonic acid, a-hydroxyglutaric; citric acid; or an aryl dioic acid such as phthalic acid, isophthalic and p-phthalic, optionally with organic substituents on the aromatic ring.

In some embodiments, the compound may be one of the following:

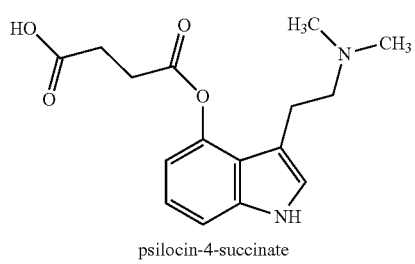
psilocin-4-succinate (1)
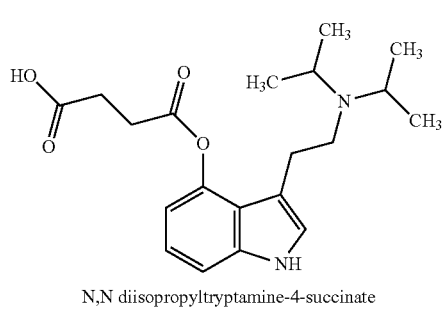
N,N diisopropyltryptamine-4-succinate (2)
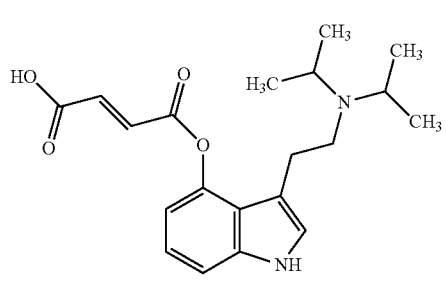
N,N diisopropyltryptamine-4-Fumarate (3)
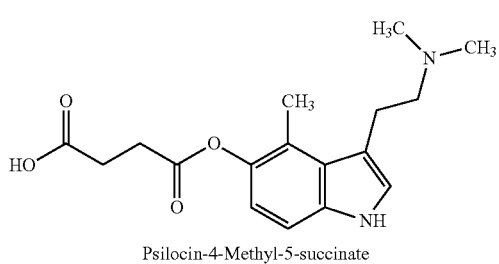
Psilocin-4-Methyl-5-succinate (4)
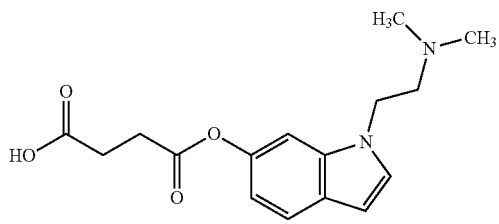
Iso-N,N dimethyltryptamine-6-succinate (5)
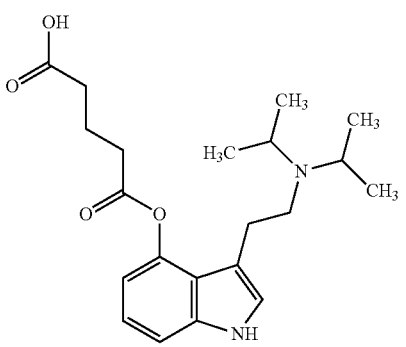
N,N diisopropyltryptamine-4-glutarate (6)
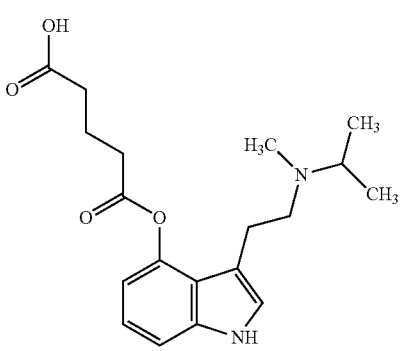
N-methyl N-isopropyltryptamine-4-glutarate (7)
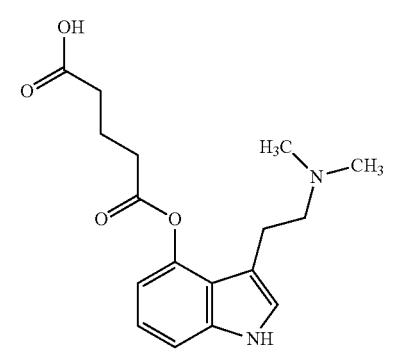
Psilocin-4-glutarate (8)
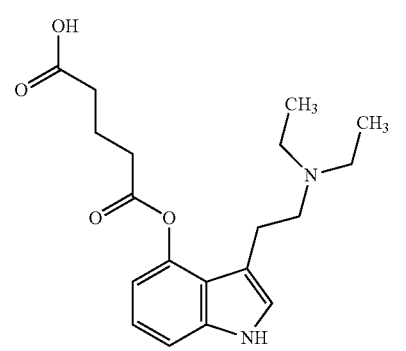
N,N diethyltryptamine-4-glutarate (9)

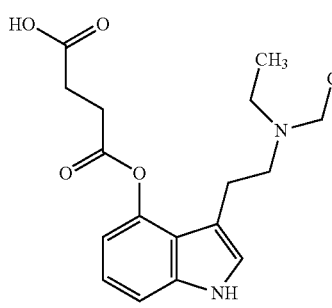

N,N diethyltryptamine-4-succinate

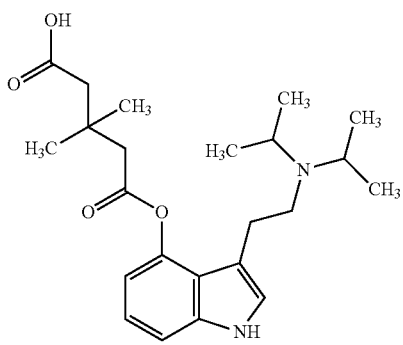

N,N diisopropyltryptamine-4-(3,3-dimethylglutarate)

In some embodiments, the diacid-modified tryptamines or isotryptamines exhibit product stability (oxidation and hydrolysis) and can be readily synthesized and purified. The diacid-modified tryptamines or isotryptamines preferably exhibit solubility in biological matrices in excess of the drug absent the diacid modification, making them superior drug candidates. As well, the diacid-modified tryptamines preferably exhibit relatively quick rates of hydrolysis in vivo, so as to convert the prodrug rapidly to the active form of the drug. This can result in improved and desirable pharmacokinetic properties with the prodrug, including more reproducible pharmacokinetic profiles. These properties can depend on the nature of the indole, the various substituents attached to the indole and the nature of the diacid ester. Stability and hydrolysis rates can be determined experimentally.

In some embodiments, the compound may comprise a carbamate ester of tryptamine, where R4 is (R9)(R10)N— where R9 and R10 define a carbamate residue and are defined as above. In some embodiments, the carbamate function comprises a zwitterionic amino-functional mono or dicarboxylic acid which is linked via the carbamate, including without limitation, zwitterionic compounds such as:

natural and unnatural neutral or anionic amino acids, such as glycine, alanine, leucine, isoleucine, serine, theonine, glutamic acid, aspartic acid;

linear alkyl α,ω-amino acids, such as 3-aminoproprionic acid, 4-amino-butyric acid;

other branched amino acids and aromatic amino acids, such as 4-amino-benzoic acid.

In some embodiments, the invention may comprise zwitterionic compounds where R4 comprises more than one non-ester carboxy function, such as the citrate derivative of a 4-hydroxytryptamine (V) or a glutamic acid carbamate of a 4-hydroxytryptamine (VI):

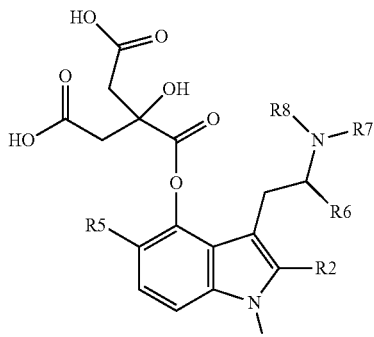

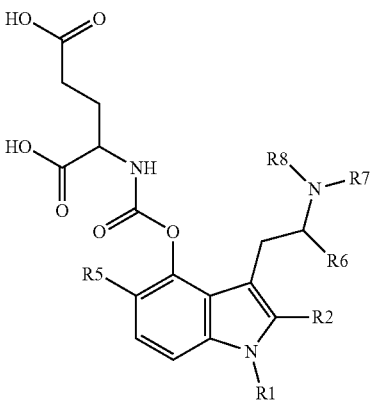

In some embodiments, the zwitterionic compound is preferably stable at neutral or slightly acidic pH. Acylation of the hydroxy functions of an indole can prevent oxidative reactions typical of substituted phenolic compounds and indoles specifically (Manevski 2010 Drug Metabolism and Disposition and Napolitano 1989 Tetrahedron), while also allowing for solubility. In some embodiments, the zwitterion has sufficient solubility (>30 mg/ml) in the range of neutral and pharmaceutically-acceptable pH values (3-8) to achieve the required potency/efficacy. Conventionally, non-prodrug pharmacophore tryptamines must be placed and held in acidic medium to achieve good solubility and stability. Acidic medium can preclude use as an injectable formulation and can cause irritation.

Embodiments of the zwitterion may also provide for convenient purification and isolation by recrystallization from common pharmaceutical solvents, such as water, methanol, ethanol, propanol or isopropanol or acetone, or mixtures thereof.

The diacid moiety is cleaved metabolically in vivo providing the active ingredient in doses and with kinetics sufficient to achieve the psychedelic state believed to be necessary for use in the treatment of depressive conditions, such as psychedelic-assisted psychotherapy. This is particularly advantageous in designing convenient medications that produce a psychedelic experience with a duration of less than 8 hours, preferably less than 6 hours, and more preferably less than 4 hours. In this sense, the requirement of hydrolysis is an additional step and therefore can reduce the speed of onset of psychoactive properties when compared to injection of the free drug (with no acylation of the hydroxy function). A slightly slower speed of onset may be preferred in some cases, so as to avoid a sudden onset which can cause anxiety, particularly in the psychedelic-naïve patient. Thus, in preferred embodiments, the speed of onset may be controlled by the rate of metabolism which can be a function of the ester and the target enzyme required for hydrolysis.

In some embodiments, certain prodrug diacid moieties, for example a succinate, may reduce the potential for abuse by inhalation or snorting. As a zwitterion, it is not likely to be absorbed rapidly through tissue devoid of esterase activity. Furthermore, the zwitterion is likely not absorbed directly by a passive mechanism into the brain. The rate of cleavage in the gut may be slower and absorption slower versus the non-acylated version and thus delay peak rates and the "rush" feeling that may be sought by persons with the intent to abuse.

Methods of Preparation

The compounds described herein can be synthesized using the methods described below, or similar methods, together with synthetic methods known in the art of synthetic organic chemistry, or by variations thereon as appreciated by those skilled in the art. Preferred methods may include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment, well within the skill of a skilled artisan, to modify the order of the synthetic steps or to select one particular process scheme over another in order to obtain a desired compound of the invention.

Protection and de-protection in the processes below may be carried out by procedures generally known in the art (see, for example, Greene, T. W. et al, *Protecting Groups in Organic Synthesis,* 3rd Edition, Wiley (1999)). General methods of organic synthesis and functional group transformations are found in: Trost, B. M. et al, eds., *Comprehensive Organic Synthesis: Selectivity, Strategy & Efficiency in Modern Organic Chemistry,* 1' Edition, Pergamon Press, New York, N.Y. (1991); March, J., *Advanced Organic Chemistry*.

4- and 5-hydroxy-tryptamines can be made by adapting methods described in the art by Baumann et al. (Beilstein 2011, 7, 442) Shulgin (The Vaults of Erowid: TiHKAL: The Chemical Story, by Alexander and Ann Shulgin) and Fricke (Eur Chem J 2019, 25, 897), as well as in U.S. Pat. No. 3,075,992 and Chen (JOC 1994, 3738).

For example, succinate prodrug compounds described herein may be prepared using the synthetic scheme as outlined in Scheme 1 starting from the corresponding hydroxy-indole and the diacid anhydride. The reaction conditions such as temperature, time, choice of solvent and workup procedures are selected which may be suitable for experimental conditions recognized by one skilled in the art. Restrictions to the substituents that are compatible with the reaction conditions will be readily apparent to one skilled in the art and alternate or analogous methods must then be used.

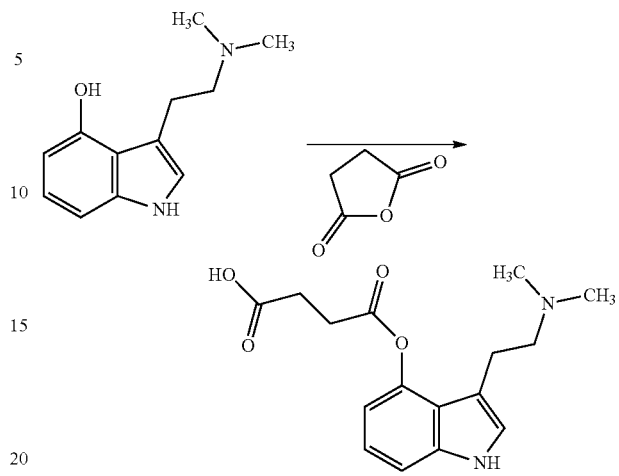

Scheme 1

Other diacid prodrugs may be prepared using other diacid anhydrides, as may be readily visualized by those skilled in the art.

A glutarate prodrug compound may be made using glutaric anhydride, using Scheme 2 below:

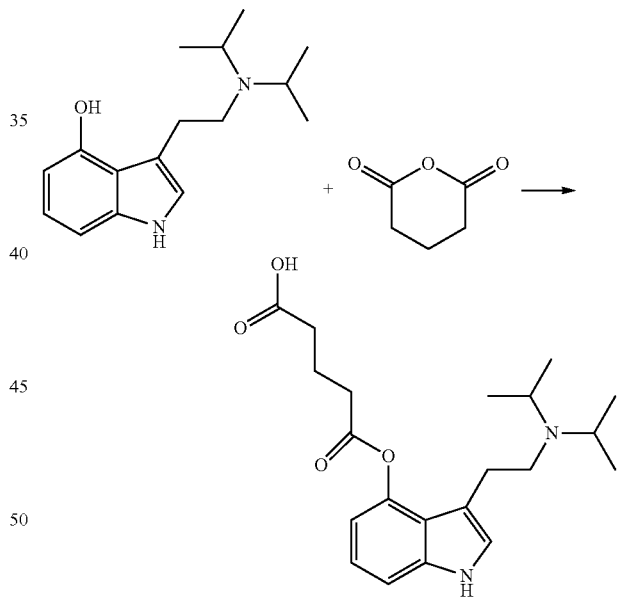

Scheme 2

One skilled in the art may readily select suitable conditions and solvents. The reaction with the diacid anhydride may take place in dichloromethane and triethylamine, or pyridine. In some embodiments, the solvent contains a base with pKa greater than 4 but less than 9. If pyridine is used, the product precipitates directly from the reaction mixture in pure form as the zwitterion.

The solid zwitterion may be converted to a suitable salt, for example, a hydrochloride salt, by addition of anhydrous HCl (gas) in a suitable solvent or by triturating in anhydrous ether HCl or dioxane HCl.

Synthesis of the diacid hemiester prodrugs may also be produced using a variety of other methods and techniques well known to those skilled in the art (Rautio, Nature Rev in Drug Discovery 2018, 17, 559), for example, using anhydride or doubly-activated forms of the diacids, such as dichloride, di-N-hydroxysuccinimide (using dicyclohexylcarbodiimide (DCC) or 1-Ethyl-3-(3-dimethylaminopropyl) carbodiimide (EDC), N-hydroxysuccinimide and DMAP), di-imizadolide (using carbonyldimidizole), or other activated form of the diacid with the hydroxy form of the active heterocyclic species. When using the diactivated forms, it is preferable to use a 2-25-fold excess of the doubly activated diacid to avoid covalently binding 2 tryptamines to the diacid.

Similarly, one skilled in the art can apply these methods to 6- or 7-hydroxy isotryptamines.

Formulations and Compositions

The invention also provides pharmaceutically acceptable compositions which comprise a therapeutically effective amount of one or more of the compounds described herein, formulated together with one or more pharmaceutically acceptable carriers (additives) and/or diluents, and optionally, one or more additional therapeutic agents. While it is possible for a compound described herein to be administered alone, it is preferable to administer the compound as a pharmaceutical composition.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, osmotic complement, preserving agents, fillers, flow regulating agents, disintegrating agents, wetting agents, emulsifying agents, suspending agents, sweetening agents, flavoring agents, perfuming agents, antibacterial agents, antifungal agents, lubricating agents, polymers, solubilizing agents, stabilizers, antioxidants and dispensing agents, depending on the nature of the mode of administration and dosage forms. Each carrier must be "acceptable" in the sense of being compatible with the other ingredients of the formulation and not injurious to the patient.

As used herein, "oral" administration includes swallowing for ingestion in the stomach or gut, and further includes lingual, sublingual, buccal and oropharyngeal administration. The compounds of this invention can be administered for any of the uses or methods described herein by any suitable means, for example, orally, such as tablets, capsules (each of which may include sustained release or timed release formulations), pills, powders, granules, elixirs, suspensions (including nano suspensions, micro suspensions, spray-dried dispersions), syrups, and emulsions; sublingually (e.g. as thin films, effervescent tablets or tablets that dissolve spontaneously under the tongue); parenterally, such as by subcutaneous, intravenous, intramuscular injection, or infusion techniques (e.g., as sterile injectable aqueous or non-aqueous solutions or suspensions); nasally, including administration to the nasal membranes, such as by inhalation spray; or rectally such as in the form of suppositories.

The dosage regimen for the compounds described herein will, of course, vary depending upon known factors, such as the pharmacokinetic and pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient; and, the effect desired. The selected dosage level may also depend on the additional factors including the activity of the particular compounds and pharmaceutical compositions described herein, whether an ester, salt or amide substituent is of the compound is used, the time of administration, the rate of excretion or metabolism of the particular compound being employed, the rate and extent of absorption, the duration of the treatment, other drugs that may be administered to the patient, compounds and/or materials used in combination with the particular compound employed and like factors well known in the medical arts.

Generally, the dosage of the prodrug for a therapy session, when used for the indicated effects, will range between about 0.001 to about 500 mg per dose, preferably between about 0.01 to about 200 mg per dose, and most preferably between about 0.1 to about 50 mg per dose, such as 10, 20, 30, 40, 50, 100 or 200 mg. Intravenously, the most preferred doses will range from about 0.01 to about 10 mg/kg/minute during a constant rate infusion.

Compounds of this invention may be administered in a single daily dose, or the total daily dosage may be administered in multiple divided doses, such as two, three, or four times daily. Alternatively, the doses may be provided on a weekly, biweekly, or monthly basis. In a preferred embodiment, only one or two doses are required for an anti-depressant effect than may extend for 1, 2, 3 or 6 months, or more.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet, dry, or melt granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0 8247 6918 X), the disclosure of which is incorporated herein by reference in its entirety.

A typical capsule for oral administration contains at least one of the compounds of the present invention (e.g. 25 mg), lactose (e.g. 75 mg), and magnesium stearate (e.g. 15 mg). The mixture is passed through a 60 mesh sieve and packed into a No. 1 gelatin capsule.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle free injectors and infusion techniques.

Parenteral formulations are typically aqueous solutions which may contain excipients such as salts, carbohydrates and pH adjusting or buffering agents (preferably to a pH of from 3.0 and 7.0, preferably 4.0 to 6.0, and more preferably 4.5 to 5.5), but, for some applications, they may be more suitably formulated as a sterile non aqueous solution or as a dried form to be used in conjunction with a suitable vehicle such as sterile, pyrogen free water or pre-fabricated, ready-to-mix aqueous buffer. Osmotic agents may be included to control tonicity.

The preparation of parenteral kits for reconstitution at point-of-care under sterile conditions, for example, by lyophilization, may readily be accomplished using standard pharmaceutical techniques well known to those skilled in the art.

A typical injectable preparation is produced by aseptically placing at least one of the compounds of the present invention (e.g. 25 mg) into a vial as a sterile filtered solution, aseptically freeze-drying and sealing. For use, the contents of the vial are mixed with e.g. 2 mL of physiological saline for injection, optionally with an appropriate amount of osmotic complements and pH adjusters to achieve a slightly acidic to neutral pH (e.g. pH 4-7), to produce an injectable preparation with low irritation but retain solubility and/or stability of the prodrug.

Compounds of the invention may be combined with soluble macromolecular entities, such as cyclodextrin and suitable derivatives thereof or polyethylene glycol containing polymers, in order to improve their solubility, dissolution rate, taste masking, bioavailability and/or stability for use in any of the aforementioned modes of administration.

Drug cyclodextrin complexes, for example, are found to be generally useful for most dosage forms and administration routes. Both inclusion and non inclusion complexes may be used. As an alternative to direct complexation with the drug, the cyclodextrin may be used as an auxiliary additive, i.e. as a carrier, diluent, or solubilizer. Most commonly used for these purposes are alpha, beta and gamma cyclodextrins, examples of which may be found in PCT Publication Nos. WO 91/11172, WO 94/02518 and WO 98/55148, the disclosures of which are incorporated herein by reference in their entireties.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

As used herein, a "therapeutically effective amount" refers to that amount of a compound being administered which will relieve to some extent one or more of the symptoms of the disorder being treated. In reference to the treatment of depression, a therapeutically effective amount refers to that amount which has the effect of reducing the severity of depression. Depression severity may be assessed using well-known structured assessment tools such as Structured Clinical Interview for DSM-5 (SCID-5) and the GRID-Hamilton Depression Rating Scale (GRID-HAMD). A therapeutically effective amount may be less than that required for a psychedelic state.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another therapy, drug, compound or pharmaceutical composition.

Therapeutic Methods and Uses

Treatment with the novel prodrugs of the present invention may substantially alleviate clinical or subclinical depression and may avoid relapse, particularly if used in combination with psychotherapy for the treatment of depression. It is known that administration of an effective dose of psilocybin produced rapid and large reductions in depressive symptoms, and many subjects achieve remission through a four-week follow up (Davis et. al.) Without restriction to a theory, it is believed that the psychedelic state is associated with the beneficial effects, however, some compounds which are 5HT2A agonists may provide the desired therapeutic effect without the psychedelic state. One aspect of the invention comprises prodrugs of those 5HT2A agonists which do provide a beneficial therapeutic state.

In general, the present invention includes the use of a compound of the present invention herein, to treat any disease or disorder which may be alleviated by a 5HT2A agonist, or the use of a compound of the present invention herein to manufacture a medicament to treat any disease or disorder which may be alleviated by a 5HT2A agonist, or a method of treating any disease or disorder which may be alleviated by a 5HT2A agonist.

In some embodiments, the invention may comprise the use of the compounds of the present invention to treat mental disorders. In some embodiments, the invention may comprise the use of the compounds of the present invention to treat depression, and particularly drug resistant depression. Other conditions that may be treated include: anxiety disorders, including anxiety in advanced stage illness e.g. cancer as well as generalized anxiety disorder, depression including major depressive disorder, postpartum depression, cluster headaches, obsessive compulsive disorder, personality disorders including conduct disorder, drug disorders including: alcohol dependence, nicotine dependence, opioid dependence, cocaine dependence and other addictions including gambling disorder, eating disorder and body dysmorphic disorder, chronic pain, or chronic fatigue.

In some embodiments, the invention may comprise a method of treating mental disorders comprising administering to a subject in need thereof a therapeutically effective amount of a compound of the present invention. In one embodiment, there is provided a method of treating depression comprising administering to a subject in need thereof therapeutically effective amount of a compound of the present invention. The depression may be drug-resistant depression or major depressive disorder.

For example, a patient diagnosed with depression may be screened prior to treatment, and then prepared for a dosing session by a trained psychotherapist. Within a dosing session, a compound of the present invention may be administered by injection of a sterile solution at a rate of 0.01-0.3 mg/kg to the patient. The patient is preferably seated for the duration of the session while being blindfolded. For safety, a trained health care professional may monitor the patient throughout the dosing session, which may last up to 12 hours. In some cases, music may be played for the patient. When the health care professional can determine that the drug substance has cleared, the psychotherapist may assist the patient with any questions relating to the psychedelic experience, and then the patient may be discharged.

To further alleviate any anxiety that may occur relative to therapy, the physician may prefer to divide the therapeutic dose and thereby reduce the initial onset of psychoactivity before applying the full complement of the dosage to achieve the full effect.

In some embodiments, treatment with a compound of the present invention may be combined with concomitant treatment with another anti-depressant drugs, either concurrently or consecutively. In preferred embodiments, treatment with a compound of the present invention is combined with psychotherapy, which may be applied prior to or after treatment. If prior to, the session may focus the patient on the intent of treatment. If after, psychotherapy is preferably performed within 48 hours of the dosing session to help the patient integrate any feelings, emotions, visions or thoughts that may have occurred during the session, as well as to allow the psychotherapist may offer advice on how best to change thinking or behavior patterns so as to improve anti-depression outcomes. Psychotherapy may continue as needed after the dosing session, for example, up to an additional 3 months, to help the patient integrate any experiences or learnings that occurred to the patient during the dosing session.

EXAMPLES

The present invention may be described with reference to the following Examples. These Examples are provided for the purpose of illustration only. All terms, names, abbreviations or acronyms are those commonly understood by those skilled in the art. Compounds shown in their zwitterionic form may readily be visualized in their neutral form by one skilled in the art, and vice versa.

Where a compound is referred to as a glutaroyl or succinoyl, or hemiglutarate or hemisuccinate, it is understood to be same as the succinate or glutarate. For example, the 4-hemiglutarate of psilocin is the same as psilocin-4-glutarate or N,N dimethyltryptamine-4-glutarate. Similarly, the 4-hemiglutarate of 4-OH-DiPT is the same as N,N diisopropyltryptamine-4-glutarate.

Example 1. 4-Hemisuccinate of Psilocin

4-Hydroxyindoles were prepared using methods or modestly adapted from methods described in the literature, such as in Kargbo 2020 ACS Omega): Accordingly, 4-acetoxyindole was reacted with oxalyl chloride in methyl-t-butyl ether (MTBE) and the resulting intermediate was quenched with dimethylamine. The indole-oxalyl-dimethylamide was reduced with Lithium Aluminum Hydride (LAH) in tetrahydrofuran (THF) to give the 4-acetoxy-3-(N,N-dimethylaminoethyl)indole, which was deprotected using aqueous base to give 4-hydroxy-dimethyltryptamine (psilocin).

The 4-hydroxytryptamine was reacted with an excess of succinic anhydride in dichloromethane (DCM) containing triethylamine, and catalyzed by N,N-dimethylaminopyridine, to give psilocin-4-succinate. A precipitate was formed which was recovered after decantation and trituration with DCM. The solid was acidified in aqueous HCl, purified by chromatography and recovered after evaporation of solvents. The structure was confirmed by NMR. Purity was determined by HPLC.

Example 2. 4-hemisuccinate of 4-hydroxy-diisopropyltryptamine (4-OH-DiPT)

4-Acetoxyindole was reacted with oxalyl chloride in MTBE and the resulting intermediate was quenched with diisopropylamine. The resulting oxalyl-amide was reduced with Lithium Aluminum Hydride (LAH) in THF to give the 4-acetoxy-3-(N,N-diisopropylaminoethyl)indole, which was in turn deprotected with aqueous base to give 4-hydroxy-3-(N,N-diisopropylaminoethyl)indole. In a 250 mL round-bottom flask containing a stir bar was added 4-OH-DiPT (5.8 g, 22.3 mmol, 1 eq.), dissolved in dichloromethane (28 mL, 5×V) and stirred at room temperature. Then succinic anhydride (1.3 eq.) was added slowly to the stirring solution, and the resulting suspension was stirred overnight at room temperature. The precipitate formed in the reaction was recovered by decantation and trituration with DCM. The solid was acidified in aqueous HCl, purified by chromatography and recovered after evaporation of solvents. The structure was confirmed by NMR. Purity was determined by HPLC.

Example 3. 4-hemifumarate of 4-OH-DiPT

4-Benzyloxyindole is reacted with oxalyl chloride in diethylether in the presence of a Friedel-Kraft catalyst and the resulting intermediate is quenched with di-isopropylamine. The resulting oxalyl-amide is reduced with Lithium Aluminum Hydride (LAH) in THF to give the 4-benzyloxy-3-(N,N-diisopropylaminoethyl)indole, which is in turn deprotected using a H2 and Pd/C to give 4-hydroxy-3-(N,N-diisopropylaminoethyl)indole. This substance is reacted with an excess of a diactivated fumaric acid (N-hydroxysuccinimide) in dichloromethane, followed by quenching any unreacted N-hydroxysuccinimide ester with aqueous acid, leaving 4-fumaroyl-3-(N,N-diisopropylaminoethyl)indole.

Example 4. 5-hemi succinate of 5-hydroxy-4-methyl-dimethyltryptamine 4-methyl-5-hydroxyindole (1) is reacted with benzyl chloride in the presence of $K_2CO_3$ in ACN to give 5-benzyloxy-4-methyl-indole, which is then reacted with oxalyl chloride in diethylether in the presence of a Friedel-Kraft catalyst and the resulting intermediate is quenched with di-methylamine. The resulting oxalyl-amide is reduced with Lithium Aluminum Hydride (LAH) in THF to give the 4-methyl-5-benzyloxy-3-(N,N-dimethylaminoethyl)indole, which is in turn deprotected using a H2 and Pd/C to give 4-methyl-5-hydroxy-3-(N,N-dimethylaminoethyl)indole. This substance is reacted with succinic anhydride in dichloromethane, catalyzed by N,N-dimethylamino-pyridine to give 4-methyl-5-succinoyl-3-(N,N-dimethylaminoethyl)indole.

Example 5. N,N dimethylisotryptamine-6-succinate

Following methods outlined in Glennon (JMedChem 1984), 6-O-Benzyl-dimethylisotryptamine is prepared by N-alkylation of 5-BzO-indole using NaH. The benzyl group is removed by catalytic hydrogenation using Pd/C/H2 to give the HO— function which is succinylated in a subsequent step using succinic anhydride, resulting in the named species.

Example 6. N,N diisopropyltryptamine-4-glutarate

In an oven-dried 50 mL round bottom flask containing 1.2 mL of anhydrous DCM was added glutaric anhydride (0.205 g, 1.8 mmol, 1.8 eq.) and the suspension was stirred under Ar. A solution of 4-OH-DiPT (0.26 g, 1 mmol, 1 eq.) in 1.5 mL anhydrous DCM was added, followed by addition of 4-dimethylaminopyridine (DMAP) (37 mg, 0.3 mmol, 0.3 eq.) and trimethylamine (0.18 mL, 1.3 eq.) and the resulting suspension was stirred overnight at r.t. under Ar.

The mixture was decanted, and the solid was triturated with anhydrous DCM (3 mL) with a few drops of anhydrous MeCN. The suspension was acidified with 1M HCl (~1.1 eq.) and concentrated to dryness. The crude product was purified by C18 reverse-phase column chromatography (40 g, A: 0.05% HCl in $H_2O$, B: 0.05% HCl in MeCN).

The structure was confirmed by NMR. Purity was determined by HPLC (>97%). The solid was resuspended in 1M HCl-dioxane to form the HCl salt which was filtered, washed with ether and dried. Yield (>95%, purity >95%; DSC endotherm 174C). The solid could be dissolved in water up to 50 mg/ml and lyophilized to form a white "cake".

Example 7. Hemiester of 3,3-dimethylglutaric acid and 4-hydroxydiisopropyltryptamine 4-Hydroxy-3-(N,N-diisopropylaminoethyl)indole was reacted with 3,3-dimethyl glutaric anhydride in pyridine to give 4-succinoyl-3-(N,N-diisopropylaminoethyl)indole with stoichiometries and parameters mentioned in example 6. A precipitate formed in the reaction was recovered by decantation and trituration in THF. The solid was washed with DCM and dried. The structure was confirmed by NMR.

Example 8. Psilocin-4-glutarate

4-Hydroxydimethyltryptamine (psilocin) was reacted with an excess of glutaric anhydride in dichloromethane (DCM) containing triethylamine to give psilocin-4-glutarate. In another example, the reaction occurred in pyridine. In either case, a precipitate was formed which was recovered after decantation and trituration with THF. The solid was washed with DCM and then dried. The structure was confirmed by NMR.

The reaction product was suspended in 1M HCl-ether to yield the corresponding HCl salt form of the product which was recovered by filtration in high yield and purity.

Example 9. HCl salt of N,N diisopropyltryptamine-4-glutarate

In a 3-neck 1 L round bottom flask under argon was added 4-OH-DiPT (31.8 g, 0.122 mol, 1 eq.), dissolved in 160 mL of anhydrous pyridine (160 mL). After stirring for 15 mins, glutaric anhydride (18.1 g, 0.158 mol, 1.3 eq.) was added in portions. The resulting suspension was stirred at r.t. overnight.

Anhydrous DCM (160 mL) was added to the suspension and it was cooled to 0° C. with for 2 h. The solid was filtered and washed with 60 mL of cold anhydrous DCM and dried overnight.

The dried solid was triturated with 160 mL of anhydrous DCM, followed by 160 mL of anhydrous THF, and then 160 mL of anhydrous DCM at 0° C. After drying, 33.0 g was obtained with 72% yield and 98.1% purity by HPLC. The structure of the zwitterion was confirmed by 1H-NMR (DMSO-d6) and MS $[M+H]^+$=375.2.

In a 100 mL round bottom flask was charged 18 mL of anhydrous diethyl ether HCl solution (4M in dioxane, 2.4 mL, 9.6 mmol, 1.2 eq.) was added slowly and stirred at r.t. for 10 mins. The zwitterion from above (3.0 g, 8.0 mmol) was added in portions and the resulting suspension was stirred for 2 h. The solid was filtered off and washed with 6 mL of $Et_2O$. The solid was dried yielding 3.16 g of the corresponding hemiester tryptamine HCl salt (96% yield, 99.0% purity by HPLC, $[M+H]^+$=375.1).

Example 10. Hemiglutarate of psilocin

Psilocin is reacted with 1.2 equivalents glutaric anhydride in warm THF to give psilocin-4-glutarate which precipitates from the reaction mixture according to methods above. The precipitate is recovered by filtration, is washed with cold 1:1 DCM/THF and dried.

Example 11. 4-Hemimalonate of 4-OH-DiPT

4-OH-DiPT was dissolved in pyridine and coupled with an excess of malonic acid and 1.2 equivalents of DCC at room temperature for 18 h. The reaction mixture was passed through a flash column (5 parts diatomaceous earth), and the first fractions containing the prodrug compound were isolated by precipitation and washing. Yield approx. 50%. Purity >95% by HPLC.

Example 12. Comparative Rates of Prodrug Hydrolysis in Serum

Pooled mixed gender human plasma (2 ml), mouse plasma, rat plasma and dog plasma were equilibrated at 37° C. The compound of example 9 was added so as to achieve a concentration of 1.0 ug/mL. Aliquots (50 uL) of the mixture were withdrawn at timed intervals (0, 0.004, 0.5, 1, 2 and 4 hours) and quenched with 200 uL of methanol/acetonitrile (1:1). The samples were vortexed and stored at −80° C. until analysis. Assays were done in triplicate. Control samples were done in phosphate buffered saline (PBS, pH 7.4) and simulated gastric fluid (SGF, pH 2). Analysis of samples as performed by HPLC-MS to determine the amounts of prodrug and drug in each sample tested. Table 1 provides the mean concentrations of prodrug remaining at different time points of the experiment. The experiment demonstrates the rapid enzymatic cleavage of the prodrug in plasma versus slow non-enzymatic hydrolysis in relevant biological media.

In some cases, Head Twitch Response (HTR) or Wet Dog Shakes (WDS) were recorded by visual observation and counting of the relevant muscle twitches. In general, the intensity of the HTR was proportional to the plasma concentration of 4-HO-DIPT with the highest intensity of head twitch occurring at the Tmax of the PK profile.

FIG. 1 show plasma concentration of 4-HO-DiPT (ng/ml) and versus time after subcutaneous administration of N,N diisopropyltryptamine-4-glutarate at a rate of 2 mg/kg.

Figure 2:
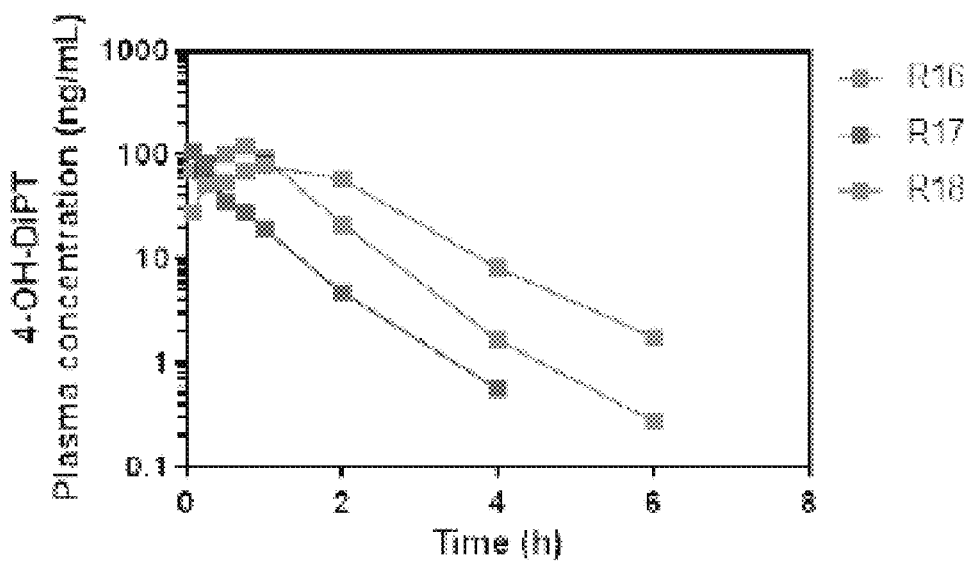
FIG. 2 is a graph showing plasma concentration of 4-HO-DiPT (ng/ml) after subcutaneous administration of N,N diisopropyltryptamine-4-glutarate at a rate of 1.4 mg/kg

Pharmacokinetics of 1.34 mg/ml 4-HO-DiPT HCl administered by intravenous or subcutaneous injection were performed in parallel under identical conditions as above. FIG. 2 shows show plasma concentration of 4-HO-DiPT (ng/ml) versus time for the different administrations. Immediately obvious is the increased variability with the active species when administered s.c. and intravenous administrations. PK parameters are shown in Table 3.

TABLE 3

PK parameters (% coefficient variation in parentheses) for 4-HO-DiPT after subcutaneous administration of N,N diisopropyltryptamine-4-glutarate (2 mg/kg).

| Route admin | Cmax, ng/ml | Tmax, h | t½, h | AUC, h*ng/ml | Bioavail-ability, % |
|---|---|---|---|---|---|
| i.v. | 458 (12) | n/a | 0.74 (22) | 152 (22) | 100% |
| s.c. | 103 (21) | 0.61 (77) | 0.67 (15) | 134 (48) | 89% |

TABLE 1

Percentage of remaining prodrug, N,N diisopropyltryptamine-4-glutarate

| Time (h) | Mouse | Rat | Dog | Human | SGF (pH2) | PBS (pH7) |
|---|---|---|---|---|---|---|
| 0 | 100 | 100 | 100 | 100 | 100 | 100 |
| 0.004 | 0 | 0 | 100 | 100 | 100 | — |
| 0.5 | 0 | 0 | 87 | 3.0 | 100 | — |
| 1 | 0 | 0 | 79 | 0.23 | 100 | — |
| 2 | 0 | 0 | 64 | 0 | — | — |
| 4 | 0 | 0 | 39 | 0 | 101 | 93 |

Example 13. Pharmacokinetics in Rats

The compound from example 9 was administered to rats by injection (intravenous and subcutaneous) with a sterile solution (2 mg/ml) at a rate of 1.4-2 mg/kg. Blood samples were taken at 15, 30, 45, 60, 120, 240 min and 360 min and analyzed by LCMS for drug and prodrug. PK profile for the prodrug and active species were obtained and relative bioavailability was determined for each of the routes of administration.

PK-PD type curves were generated to demonstrate the activity of the drug (FIGS. 1 and 2). In rodent, prodrug was not observed, as it was rapidly converted to the active form. Relevant PK parameters for i.v. and s.c administrations 4-HO-DiPT were determined and are shown in Table 2:

TABLE 2

PK parameters (% coefficient of variation in parentheses) for 4-HO-DiPT after subcutaneous administration of N,N diisopropyltryptamine-4-glutarate (2 mg/kg).

| Route admin | Cmax (ng/ml) | Tmax (h) | t½ (h) | AUC h*ng/ml | Bioavail-ability (%) |
|---|---|---|---|---|---|
| i.v. | 305 (9.8) | n/a | 0.601 (3.3) | 146 (3.1) | 97 (3.1)* |
| s.c. | 150 (30) | 1.0 (0) | 0.67 (0.1) | 203 (21) | n/a |

Based on PK parameters from the i.v. administration of 4-HO-DIPT

Example 17. Pharmacokinetics in Human Volunteers

The compound from example 6 (N,N diisopropyltryptamine-4-glutarate) is administered to human volunteers by subcutaneous injection of a sterile solution (1 mg/ml) at a dosage of 0.1-0.6 mg/kg. Blood samples are taken at 5, 15, 30, 45, 60, 120, 240 and 480 min and 24 h. Samples are analyzed by LCMS for drug and prodrug. Subjective effects are measured using standardized questionnaires. The PK analysis shows a maximal plasma concentration (CMax) at approx. 45 min after the injection. Subjective effects show an intensity of psychoactivity that correlates with blood levels.

The compound from example 2 (4-hemisuccinate of 4-OH-DiPT) is administered to human volunteers by oral ingestion of a tablet containing 50 mg of the prodrug. Blood samples are taken at 5, 15, 30, 45, 60, 120, 240 and 480 min and 24 h. Samples are analyzed by LCMS for drug and prodrug. Subjective effects are measured using standardized questionnaires. The PK analysis shows a CMax at approx. 90 min for the injection. Subjective effects show an intensity of psychoactivity that correlates with blood levels.

Example 18. Use in Treatment

The compound of example 6 (N,N diisopropyltryptamine-4-glutarate) is administered by i.m. or s.c. injection (ca. 25 mg; 0.4-0.5 mg/kg) to a human patient suffering depression, or by oral administration (ca. 50-200 mg; 0.8-3.2 mg/kg) with tablets. In another example of use, the compound of example 6 (4-hemiglutarate of 4-OH-DiPT) is similarly administered. Prior to the dosing session, the patient is qualified for the experience by measurement of depression scores, screened for exclusions (e.g. history of psychoses, unfavorable heart condition, pregnancy) and finally, the patient is encouraged to formulate an intent for the dosing session. Dosing is performed in a quiet clinic setting with the patient resting comfortably in an inclined, but unrestrained, position to avoid falls. The patients' eyes are covered, and music is applied. The drug is administered. After 4 h, the patient reports no longer feeling the effects of the drug and is asked to sit up while under supervision. Feeling normal, the patient is allowed to stand (supervised) and feeling in control, is allowed to move around. One hour later, the patient is discharged. Later by 24 h, the patient returns to the clinic to meet with a psychotherapist to recount the session. The patient records a depression score via questionnaire and is again discharged. At regular intervals the patient is consulted for recurrence of depressive symptoms.

Example 19. Injectable Formulation Kit

A vial is prepared with 25 mg of compound in Example 6 as a hydrochloride salt (sterilized powder or lyophilizate). In a separate vial is placed 1 ml of a sterile filtered solution containing 70 mM $Na_2HPO_4$. The final pH of the solution is 4.0-5.0. These 2 components constitute a kit for reconstitution of a drug product for subcutaneous injection at point of care.

REFERENCES

All publications, patents, patent applications, etc. mentioned in the above specification are incorporated herein by reference in their entireties, including the following:
1. American Psychiatric Association. (2013). *Diagnostic and statistical manual of mental disorders* (5th Ed.). https://doi.org/10.1176/appi.books.9780890425596
2. Anderson, W. K., & Mulumba, B. (1984). Synthesis of Methyl 2,3-bis(hydroxymethyl)-5-phenyl-7-oxabicyclo[2.2.1]hepta-2,5-diene-6-carboxylatebis(N-methylcarbamate) derivatives as potential antitumor agents. *Journal of pharmaceutical sciences,* 73(8), 1182-1183. https://doi.org/10.1002/jps.2600730844
3. Anderson, B. D., Conradi, R. A., & Lambert, W. J. (1984). Carboxyl group catalysis of acyl transfer reactions in corticosteroid 17- and 21-monoesters. *Journal of pharmaceutical sciences,* 73(5), 604-611. https://doi.org/10.1002/jps.2600730507
4. Bahar, F. G., Ohura, K., Ogihara, T., & Imai, T. (2012). Species Difference of Esterase Expression and Hydrolase Activity in Plasma. *Journal of Pharmaceutical Sciences,* 101(10), 3979-3988. https://doi.org/10.1002/jps.23258
5. Baumann, M., Baxendale, I. R., Ley, S. V., & Nikbin, N. (2011). An overview of the key routes to the best selling 5-membered ring heterocyclic pharmaceuticals. *Beilstein Journal of Organic Chemistry,* 7, 442-495. https://doi.org/10.3762/bjoc.7.57
6. Carhart-Harris, R. L., Roseman, L., Haijen, E., Erritzoe, D., Watts, R., Branchi, I., & Kaelen, M. (2018). Psychedelics and the essential importance of context. *Journal of Psychopharmacology,* 32(7), 725-731. https://doi.org/10.1177/0269881118754710
7. Chen, C.-yi, Senanayake, C. H., Bill, T. J., Larsen, R. D., Verhoeven, T. R., & Reider, P. J. (1994). Improved Fischer Indole Reaction for the Preparation of N,N-Dimethyltryptamines: Synthesis of L-695,894, a Potent 5-HT1D Receptor Agonist. *The Journal of Organic Chemistry,* 59(13), 3738-3741. https://doi.org/10.1021/jo00092a046
8. Davis A K, Barrett F S, May D G, et al. Effects of Psilocybin-Assisted Therapy on Major Depressive Disorder: A Randomized Clinical Trial. JAMA Psychiatry. 2021; 78(5):481-489. doi:10.1001/jamapsychiatry.2020.3285
9. Ebenezer, I. S. (2015). Affective Disorders: Depression in Neuropsychopharmacology and Therapeutics, Chapter 6 *Neuropsychopharmacology and therapeutics*. John Wiley & Sons Inc.
10. First, M. B., W., W. J. B., Karg, R. S., & Spitzer, R. L. (2016). *Scid-5-Cv: structured clinical interview for Dsm-5 disorders, clinician version*. American Psychiatric Association Publishing.
11. Fricke, J., Lenz, C., Wick, J., Blei, F., & Hoffmeister, D. (2018). Production Options for Psilocybin: Making of the Magic. *Chemistry—A European Journal,* 25(4), 897-903. https://doi.org/10.1002/chem.201802758
12. Glennon, R. A., Jacyno, J. M., Young, R., Mckenney, J. D., & Nelson, D. (1984). Synthesis and Evaluation of a Novel Series of N,N-Dimethylisotryptamines. *Chemischer Informationsdienst,* 15(24). https://doi.org/10.1002/chin.198424187
13. Hofmann A, Troxler F. Esters of indoles. U.S. Pat. No. 3,075,992 and Process for the production of new esters of the indole series Swiss Patent No. 386422.
14. International Society for CNS Drug Development. (2003). GRID-HAMD-17 *Structured Interview Guide*. ISCDD.
15. Kargbo, R. B., Sherwood, A., Walker, A., Cozzi, N. V., Dagger, R. E., Sable, J., O'Hern, K., Kaylo, K., Patterson, T., Tarpley, G., & Meisenheimer, P. (2020). Direct Phosphorylation of Psilocin Enables Optimized cGMP Kilogram-Scale Manufacture of Psilocybin. ACS Omega, 5(27), 16959-16966. https://doi.org/10.1021/acsomega.0c02387
16. Lieberman, H. A., & Lachman, L. (1980). *Pharmaceutical dosage forms—tablets,* vol. 1. Marcel Dekker.
17. Luethi, D., & Liechti, M. E. (2018). Monoamine Transporter and Receptor Interaction Profiles in Vitro Predict Reported Human Doses of Novel Psychoactive Stimulants and Psychedelics. *International Journal of Neuropsychopharmacology,* 21(10), 926-931. https://doi.org/10.1093/ij np/pyy047
18. Manevski, N., Kurkela, M., Hoglund, C., Mauriala, T., Court, M. H., Yli-Kauhaluoma, J., & Finel, M. (2010). Glucuronidation of psilocin and 4-hydroxyindole by the human UDP-glucuronosyltransferases. *Drug metabolism and disposition: the biological fate of chemicals,* 38(3), 386-395. https://doi.org/10.1124/dmd.109.031138
19. Napolitano, A., d'Ischia, M., Prota, G., Schultz, T., & Wolfram, L. (1989). Oxidation of 4,6- and 7-hydroxyindoles. *Tetrahedron,* 45, 6749-6760.
20. Rautio, J., Meanwell, N. A., Di, L., & Hageman, M. J. (2018). The expanding role of prodrugs in contemporary drug design and development. Nature reviews. *Drug discovery,* 17(8), 559-587. https://doi.org/10.1038/nrd.2018.46
21. Shulgin, A. T., & Shulgin, A. (2017). *Tihkal: the continuation*. Transform Press.

22. Silverman, R. B., & Holladay, M. W. (2014). Prodrugs and Drug Delivery Systems. *The organic chemistry of drug design and drug action*. Elsevier Academic Press.
23. Watts, R., & Luoma, J. B. (2020). The use of the psychological flexibility model to support psychedelic assisted therapy. *Journal of Contextual Behavioral Science*, 15, 92-102.
24. Patent Nos. GB942548, GB912714 and U.S. Pat. No. 9,630,941

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated. To the extent that the following description is of a specific embodiment or a particular use of the invention, it is intended to be illustrative only, and not limiting of the claimed invention.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to combine, affect or connect such aspect, feature, structure, or characteristic with other embodiments, whether or not such connection or combination is explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an element, item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all ranges described herein, and all language such as "between", "up to", "at least", "greater than", "less than", "more than", "or more", and the like, include the number(s) recited and such terms refer to ranges that can be subsequently broken down into sub-ranges as discussed above.

What is claimed is:
1. A compound of Formula (I) (II), (III) or (IV) or a pharmaceutically acceptable salt or zwitterion thereof:

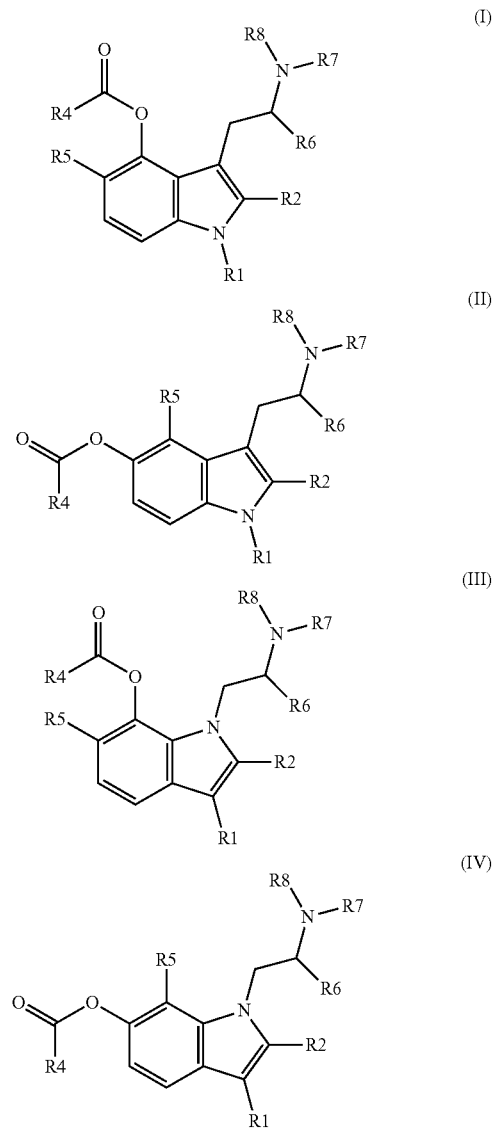

wherein:
(1) R1, R2, and R6 are each independently selected from hydrogen, linear or branched alkyl, or arylalkyl;
(2) R4 is
   a. —X—CO2H, where X is a linear, cyclic or branched, saturated or unsaturated carbon chain, optionally substituted with —OH or —CO2H; or an aromatic ring, optionally substituted with alkyl or CO2H; or
   b.

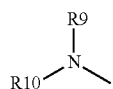

wherein R9 is X—CO2H, where X is as defined in (2)(a) above and R10 is linear or branched alkyl or arylalkyl, optionally substituted by —OH or —CO2H;
(3) R5 is hydrogen, linear or branched alkyl, arylalkyl, or O—R5', where R5' is hydrogen, linear or branched alkyl; and
(4) R7 and R8:
   c. are each independently selected from hydrogen, linear or branched alkyl, or arylalkyl, with the proviso that each of R7 and R8 is not hydrogen, or
   d. together form a non-aromatic N-containing heterocycle, optionally substituted with alkyl.

2. The compound of claim 1, selected from the group consisting of:

(1)

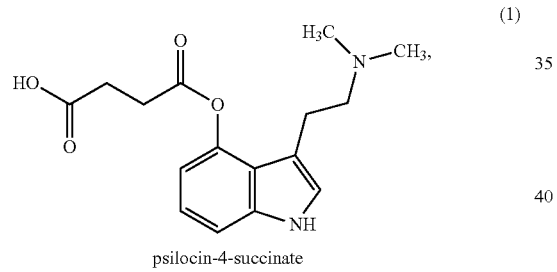

psilocin-4-succinate (2)

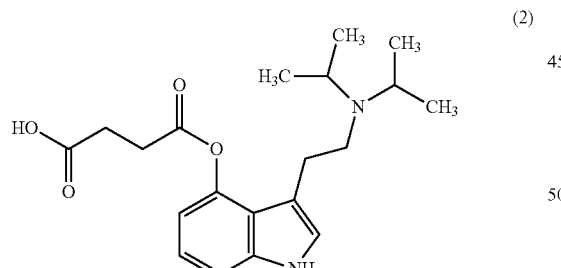

N,N diisopropyltryptamine-4-succinate (3)

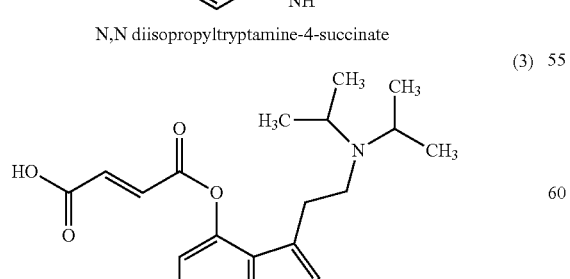

N,N diisopropyltryptamine-4-Fumarate (4)

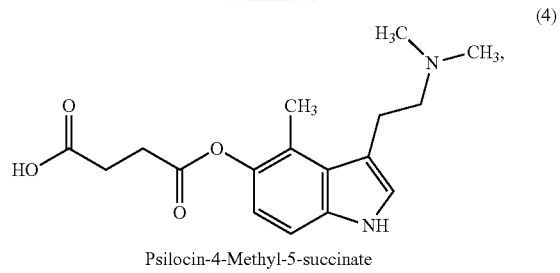

Psilocin-4-Methyl-5-succinate (5)

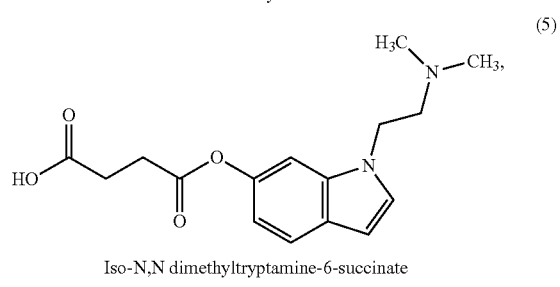

Iso-N,N dimethyltryptamine-6-succinate (6)

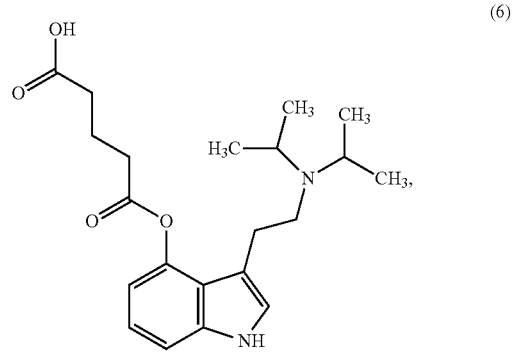

N,N diisopropyltryptamine-4-glutarate (7)

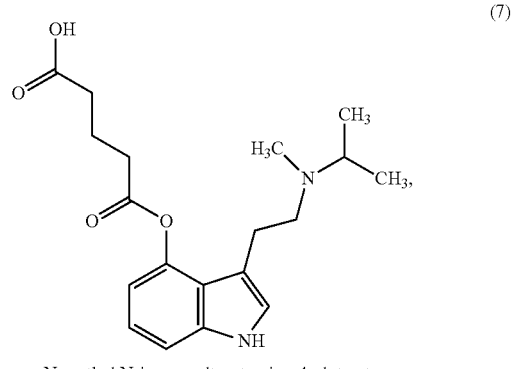

N-methyl N-isopropyltryptamine-4-glutarate (8)

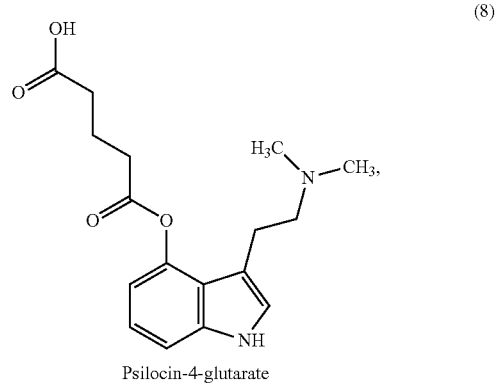

Psilocin-4-glutarate

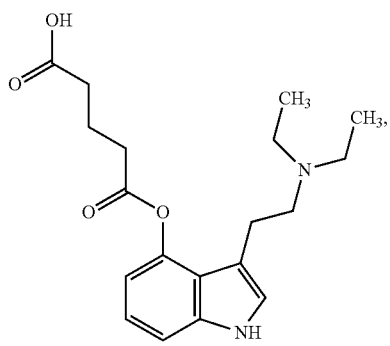

N,N diethyltryptamine-4-glutarate

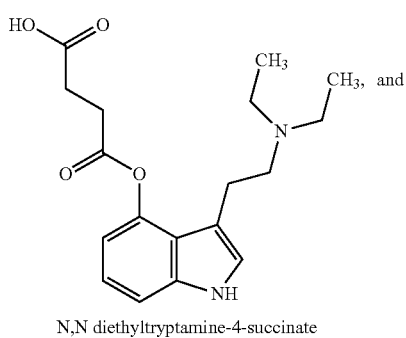

N,N diethyltryptamine-4-succinate

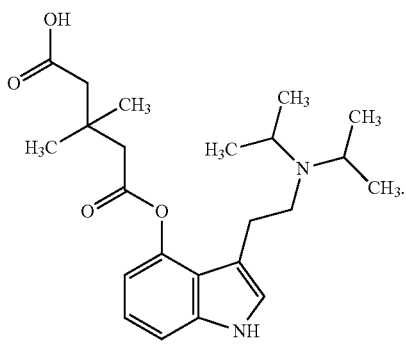

N,N diisopropyltryptamine-4-(3,3-dimethylglutarate)

3. The compound of claim 1 wherein:
(1) R1, R2, and R6 are each independently selected from H or linear $C_{1-5}$ alkyl;
(2) R4 is —X—CO2H, where X is a linear or branched $C_{1-5}$ carbon chain, optionally substituted with OH or CO2H;
(3) R5 is hydrogen, linear or branched $C_{1-5}$ alkyl, arylalkyl, or O-R5', where R5' is hydrogen, linear or branched $C_{1-5}$ alkyl; and/or
(4) R7 and R8 are each independently selected from H or linear or branched $C_{1-5}$ alkyl, with the proviso that each of R7 and R8 is not hydrogen.

4. The compound of claim 3 wherein R7 and R8 are the same or different, and are linear or branched $C_{1-4}$ alkyl.

5. The compound of claim 4 wherein R7 and R8 are each methyl or isopropyl.

6. The compound of claim 3 wherein X is a linear C1-C3 chain, optionally substituted with OH or CO2H.

7. The compound of claim 5 wherein X is a linear C3 chain.

8. The compound of claim 7 wherein R7 and R8 are both methyl, or R7 and R8 are both isopropyl, or one of R7 and R8 is methyl and the other is isopropyl.

9. A composition comprising a compound of claim 1, and a pharmaceutically acceptable excipient.

10. The composition of claim 9 comprising an oral dosage formulation or an injectable formulation.

11. The composition of claim 10 which is a solution for injection.

12. The composition of claim 11 wherein the solution has a pH of between about 3.0 and 7.0, preferably 4.0 to 6.0, and more preferably 4.5 to 5.5.

13. A method of treating a mental disorder, comprising the step of administering an effective amount of a compound of claim 1.

14. The method of claim 13 wherein the mental disorder is depression.

15. A method of making a compound of formula (I), (II), (III) or (IV) in claim 1 comprising reacting a tryptamine with a cyclic anhydride in a suitable anhydrous solvent, wherein the tryptamine is hydroxytryptamine or hydroxyisotryptamine.

16. The method of claim 15, wherein the solvent contains a base with pKa greater than 4 and less than about 9, and the resulting compound is isolated as a zwitterion.

17. The method of claim 16 wherein the solvent is pyridine.

18. The method of claim 17 wherein the compound is a compound of claim 2.

19. The method of claim 15 wherein the tryptamine is 4-OH diisopropyltryptamine or psilocin and the cyclic anhydride is succinic anhydride or glutaric anhydride.

20. N,N diisopropyltryptamine-4-glutarate or a pharmaceutically acceptable salt or zwitterion thereof.

21. A method of treating a mental disorder, comprising the step of administering an effective amount of a compound of claim 20.

22. The method of claim 21 wherein the mental disorder is depression.

23. A compound of Formula (I) or (III) or a pharmaceutically acceptable salt or zwitterion thereof:

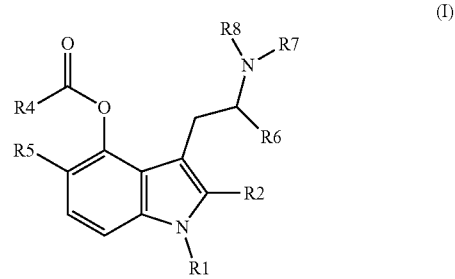

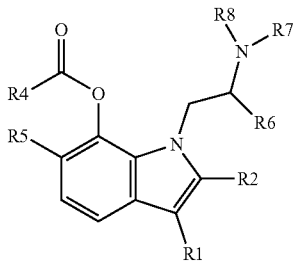

wherein:
(1) R1, R2, and R6 are each independently selected from hydrogen, linear or branched alkyl, or arylalkyl;

(2) R4 is
- a. (—X—CO2H, where X is a linear, cyclic or branched, saturated or unsaturated carbon chain, optionally substituted with —OH or —CO2H; or an aromatic ring, optionally substituted with alkyl or CO2H; or
- b.

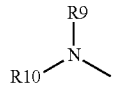

wherein R9 is X13 CO2H, where X is as defined in (2)(a) above and R10 is linear or branched alkyl or arylalkyl, optionally substituted by —OH or —CO2H;
- (3) R5 is hydrogen, linear or branched alkyl, arylalkyl, or O—R5', where R5'- is hydrogen, linear or branched alkyl; and
- (4) R7 and R8:
  - c. are each independently selected from hydrogen, linear or branched alkyl, or arylalkyl, or
  - d. together form a non-aromatic N-containing heterocycle, optionally substituted with alkyl.

* * * * *